United States Patent [19]

Nagel et al.

[11] Patent Number: 4,914,207

[45] Date of Patent: Apr. 3, 1990

[54] ARYLTHIAZOLYLIMIDAZOLES

[75] Inventors: Arthur A. Nagel; James P. Rizzi; Terry J. Rosen, all of Groton, Conn.

[73] Assignee: Pfizer Inc., New York, N.Y.

[21] Appl. No.: 349,278

[22] Filed: May 9, 1989

[51] Int. Cl.4 .................. C07D 417/04; C07D 417/14
[52] U.S. Cl. .................................... 546/167; 546/278; 548/202
[58] Field of Search ................. 546/167, 278; 548/202

[56] References Cited

U.S. PATENT DOCUMENTS 3,786,061  1/1974  Novello et al. ..................... 548/202
3,801,590  4/1974  Oraber et al. ....................... 548/202

Primary Examiner—David B. Springer
Attorney, Agent, or Firm—Peter C. Richardson; J. Trevor Lumb; James M. McManus

[57] ABSTRACT

Arylthiazolylimidazoles as 5HT$_3$ antagonists useful in the treatment of nausea, anxiety, pain, schizoprenia and gastrointestinal disorders.

11 Claims, No Drawings

ARYLTHIAZOLYLIMIDAZOLES

BACKGROUND OF THE INVENTION

This invention relates to novel arylthiazolylimidazoles which are antagonists at the serotonin $5HT_3$ receptor and useful as anti-emetic agents in warm blooded animals, particularly the emesis caused by administration of the anticancer drug cisplatin. In addition, the compounds of the present invention are useful in the treatment of schizophrenia, anxiety, pain and gastrointestinal disorders.

Compounds recognized for their ability to act as antagonists at the serotonin $5HT_3$ receptor sites are described in U.S. Pat. Nos. 4,593,034 and 4,749,718 and U.K. patent application Ser. Nos. 2,125,398A, 2,166,726A, 2,166,727A, 2,166,728A and 2,193,633A.

SUMMARY OF THE INVENTION

The novel arylthiazolylimidazoles of the present invention are of formula I:

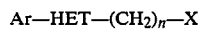

or a pharmaceutically acceptable acid addition salt thereof, wherein Ar is methoxynaphthyl, pyridyl, 3-indolyl, 1-methyl-3-indolyl, 1-benzyl-3-indolyl, 8-quinolyl, phenyl or mono or disubstituted phenyl wherein said substituent is each alkyl of one to three carbon atoms, hydroxy, alkoxy of one to three carbon atoms, fluoro, chloro, bromo or trifluormethyl; n is an integer of 1 or 2; HET is thiazolyl; and X is imidazole, mono- or dimethylimidazole, 2-benzimidazole or phenylimidazole.

A preferred group of compounds are those wherein Ar is phenyl or monosubstituted phenyl wherein said substituent is alkyl of one to three carbon atoms, hydroxy, alkoxy of one to three carbon atoms, fluoro, chloro, bromo or trifluoromethyl and n is 1. Especially preferred within this group are the compounds 4-(4'-phenylthiazol-2'-ylmethyl)-5-methylimidazole, 4-(4'-[o-methoxyphenyl]thiazol-2'-ylmethyl)-5-methylimidazole, 4-(4'-[p-fluorophenyl]thiazol-2'-ylmethyl)-5-methylimidazole, 4-(4'-[o-ethoxyphenyl]thiazol-2'-ylmethyl)-5-methylimidazole, 4-(2'-[o-methoxyphenyl]thiazole-4'-ylmethyl)-5-methylimidazole and 4-(4'[o-fluorophenyl]thiazol-2'-ylmethyl)-5-methylimidazole.

A second preferred group of compounds of the present invention are those wherein n is 1 and X is 5-methylimidazol-4-yl. Especially preferred within this group are 4-(4'-[quinol-8''-yl]thiazol-2'-ylmethyl)-5-methylimidazole and 4-(4'-[indol-3''-yl]thiazol-2'-ylmethyl)-5-methylimidazole.

As previously indicated, the present invention embraces pharmaceutically acceptable salts of the biologically active compounds. Such salts are those which are non-toxic at the dosages administered. Since compounds of the invention contain basic groups, acid addition salts are possible. Pharmaceutically acceptable acid addition salts include e.g., the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate, glutamate, aspartate and saccharate salts.

DETAILED DESCRIPTION OF THE INVENTION

Compounds of the present invention wherein HET is a 4-thiazol-2-yl moiety are readily prepared by reacting a thioamide or acid addition salt thereof with a halomethyl ketone as follows:

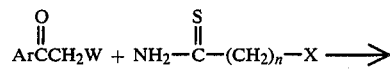

W = Cl or Br

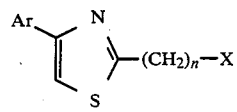

The reaction is conveniently carried out by reacting equimolar amounts of the halomethyl ketone and the thioamide in a reaction-inert solvent such as a lower alkanol of one to three carbon atoms. The reaction time is dependent on the reaction temperature and inherent reactivity of the starting reagents. In general, the reaction time can vary between a few hours to overnight at reflux temperature of the reaction solvent.

The product can be isolated as an addition salt by removing the reaction solvent and purifying the residual product. Alternately, the residual product as an acid addition salt can be partitioned between water and a water-immiscible solvent such as ethyl acetate and the aqueous phase made basic to a pH of about 9–9.5, thereby neutralizing the acid addition salt and allowing the desired product to dissolve in the organic phase. The organic phase can be separated and evaporated to provide the desired product as a free base.

The isolated product can be purified by known methods, the most common being by recrystallization or column chromatography on silica gel.

The free base product can be converted to a salt by treating a solution of said product with at least an equimolar amount of the appropriate acid. The use of two moles of acid per mole of free base product can result in the formation of a double salt, i.e., a dihydrochloride, etc.

The synthesis of the 5-thiazol-2-yl positional isomeric compound is achieved by a similar type of condensation using, in place of the halomethyl ketone, on alpha-haloacetaldehyde, as follows:

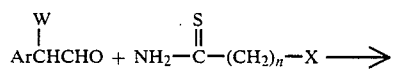

W = Cl, Br

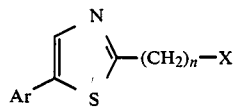

The reaction media, reaction time and temperature, isolation and purification of the products are analogous to those described for the halo ketone reaction.

Synthesis of the corresponding 2-thiazol-4-yl isomer is carried out by C-alkylation of lithium imidazole using a 2-aryl-4-haloalkylthiazole, as follows:

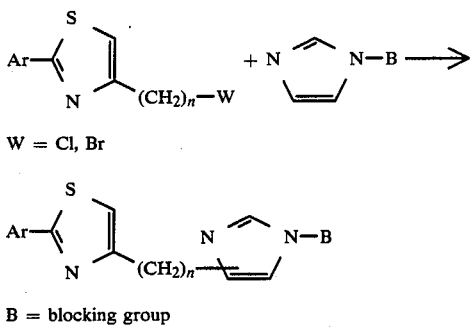

W = Cl, Br

B = blocking group

The appropriate imidazole, blocked at the $N^1$-nitrogen to prevent N-alkylation, is treated with one mole of butyl lithium at about −70° C. in tetrahydrofuran, as the reaction solvent, followed by the addition of the requisite 2-aryl-4-haloalkylthiazole. Under the conditions of employing only an N-blocked imidazole, alkylation proceeds at the $C_2$-carbon. If the $C_2$-carbon is also blocked, as with a trimethylsilyl group, the C-alkylation proceeds at the $C_5$-carbon. A substituent at the $C_5$-position, such as a methyl group, shifts the alkylation to the $C_4$-carbon.

Following the addition of the appropriate 2-aryl-4-haloalkylthiazole, the reaction mixture is maintained at −70° C. for 30 minutes to two hours. The reaction is quenched with water and the reaction mixture concentrated to dryness. The product is isolated by partitioning it between water and a water-immiscible solvent. The product, isolated from the organic phase, is purified by the methods previously mentioned.

In a similar manner the corresponding 2-thiazol-5-yl isomers are prepared by C-alkylation of a lithium imidazole using a 2-aryl-5-haloalkylthiazole. The reaction temperatures, times, isolation and purification are similar to the 2,4-isomeric product.

As indicated previously, alkylation can be carried out on a nitrogen of an imidazole by the simple alkylation with a 2-aryl-4- or -5-haloalkylthiazole employing a simple alkali metal salt of said imiazole in a reaction-inert solvent. For the purpose of N-alkylation, a solution of the imidazole in an aprotic solvent such as dimethylformamide is treated with an equimolar amount of sodium hydride, followed by the addition of an equimolar amount of the appropriate halide. The product is obtained by quenching the reacton mixture in water followed by extraction of the product with a water immiscible solvent. Purification is by conventional means as previously discussed.

Compounds of the present invention having an N-methylated imidazole in the structure are prepared either by starting with such an N-methylated moiety already in the structure of one of the starting reagents or by the N-methylation of a compound of the present invention having an imidazole structure which possesses an alkylatable NH site.

This latter procedure comprises adding methylating agent, such as methyl iodide, to a solution consisting of an equimolar amount of the appropriate compound to be methylated and an equimolar molar amount of sodium carbonate in water containing sufficient tetrahydrofuran to solubilize the starting reagent. At a reaction temperature of 0°–5° C. the reaction is complete in 3–4 hours. The product is isolated by quenching the reaction mixture in water followed by extraction with a water-immiscible solvent. Purification of the product, including the separation of any positional isomers resulting the alkylation on different tautomeric forms of the imidazole.

The intermediates used in the synthesis of the compounds of the present invention are described herein or can be prepared by procedures which are available from the literature.

As previously mentioned, the compounds of the instant invention are antagonists of 5-hydroxytryptamine (5HPT) at the $5HT_3$ receptors. This is demonstrated by their ability to antagonize the effects of 5HT in the Bezold-Jarisch reflex [Richardson, et al., Nature 316, 126 (1985)] and their ability to bind to 5HT receptors in brain tissue [Watling, et al., European J. Pharmacol. 149, 397 (1988)]. The compounds of the present invention are especially useful in controlling emesis due to administration of platinum anti-cancer agents. Evaluation of these compounds as anti-emetic agents against cisplastin uses the procedure in Cylys, Res. Commun. Chem. Pathol. Pharmacol., 23, 61 (1979).

The compounds of the present invention can be administered as antiemetic agents by either the oral or parenteral routes of administration, with the former being preferred for reasons of patient convenience and comfort. In general, these antiemetic compounds are normally administered orally in dosages ranging from about 5 mg to about 10 mg per kg of body weight per day and 0.1 mg to about 1.0 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

EXAMPLE 1

4-(4'-[Quinol-8"-yl]thiazol-2'-ylmethyl)-5-methylimidazole (Ar=quinol-8-yl; HET=4-thiazol-2-yl; n=1; and X=5-methylimidazol-4-yl)

A. 8-Chlorocarbonylquinoline hydrochloride

Quinoline-8-carboxylic acid (1.0 g) was added to 3 ml of thionyl chloride, and the reaction mixture heated at reflux for one hour. The reaction mixture was allowed to stir at room temperature and was then concentrated in vacuo. The residue was washed with benzene (2×10 ml) and was used in the next reaction.

B. 8-Chloromethylcarbonylquinoline

To 12 ml of a 40% aqueous potassium hydroxide solution and 50 ml of diethyl ether at 0° C. was added slowly with shaking 40 g of 1-methyl-N'-nitro-N-nitrosoquanidine. The ether layer was decanted into a second flask containing potassium hydroxide pellets at 0° C. The ether was again decanted from the solids into a third flask at 0° C. 8-Chlorocarbonylquinoline hydrochloride (1.57 g) was added to the ether solution and the reaction mixture allowed to stand at 0° C. until the bubbles ceased forming when the flask was shaken. Ether saturated with hydrogen chloride was added until the pH of the reaction mixture was acidic. Water was added (50 ml) and the pH raised to 8 with aqueous sodium hydroxide solution. The product was extracted with ethyl acetate and the organic phase dried over sodium sulfate and concentrated in vacuo. The residue was dissolved in ethyl acetate, washed with a saturated sodium bicarbonate solution and concentrated under vacuum, 500 mg.

C.
4-(4'-[Quniol-8"-yl]thiazol-2"-ylmethyl-5-methylimidazole

The product of Example 1B (500 mg) and 376 mg of 2-(4'-methylimidazol-5'-yl)thioacetamide in 50 ml of i-propanol was heated at reflux for 48 hours. Thye solvent was removed in vacuo and the residue partitioned between water (50 ml) and ethyl acetate. The pH was adjusted to 9 with aqueous sodium hydroxide and the organic layer separated, dried and concentrated to a brown oil, 47 mg. The residue was dissolved in ethyl acetate and treated with an ether solution of hydrogen chloride. The resulting suspension was concentrated to dryness and treated with chloroform. This solution was concentrated in vacuo and the residue triturated with hexane and filtered, m.p. >210° C.

The NMR spectrum (CDCl$_3$) showed absorption at 2.14 (s, 3H), 4.24 (s, 2H), 7.25 (m, 2H), 7.44 (m, 2H), 7.67 (d, 1H), 8.35 (d, 1H), 8.38 (s, 1H) and 8.80 (m, 1H) ppm.

EXAMPLE 2

4-(4'-[p-Methoxyphenyl]thiazol-2'-ylmethyl)-5-methylimidazole (Ar=p-CH$_3$OC$_6$H$_4$; HET=4-thiazol-2-yl; n=1; and X=5-methylimidazol-4-yl)

A solution of 250 mg of p-methoxyphenacyl bromide and 209 mg of 2-(4'-methylimidazol-5'-yl)thioacetamide hydrocloride in 3 ml of isopropanol was heated at 80° C. for 2 hours. The reaction mixture was cooled and a small amount of chloroform and diethyl ether was added to the resulting suspension. The solids were filtered (142 mg) and added to 5 ml of water. After the water was extracted with chloroform (3×5 ml), the pH of the aqueous solution was adjusted to 7.5 with a saturated aqueous sodium bicarbonate solution and extracted several times with chloroform. The extracts were combined, dried over sodium sulfate and concentrated to a white solid, 120 mg, m.p. 165°–166° C.

The NMR (300 MHz, CDCl$_3$) spectrum showed absorption at 2.36 (s, 3H), 3.93 (s, 3H), 4.38 (s, 2H), 7.00 (d, J=9 Hz, 2H), 7.32 (s, 1H), 7.57 (s, H) and 7.85 (d, J=9 Hz, 2H) delta.

EXAMPLE 3

4-(4'-[o-Hydroxyphenyl]thiazol-2'-ylmethyl)-5-methylimidazole (Ar=o-HOC$_6$H$_4$; HET=4-thiazol-2-yl; n=1; and X=5-methylimidazol-4-yl)

Starting with 150 mg of o-hydroxyphenacyl bromide and 134 mg of 2-(4'-methylimidazol-5'-yl)thioacetamide hydrochloride in 5 ml of isopropanol and using the procedure of Example 2, there was obtained, after a 3 hour reaction time, 120 mg of the titled product as the free base. The product was purified by flash column chromatography on 5 g of silica gel (methanol-chloroform, 10:90-v:v) to give 110 mg of product as a white solid.

The NMR (300 MHz, DMSO-d$_6$) spectrum showed absorption at 2.21 (s, 3H), 4.26 (s, 2H), 6.92 (m, 2H), 7.20 (t, J=5 Hz, 1H), 7.48 (s, 1H), 7.95 (d, J=7 Hz, 1H) and 8.01 (s, 1H) delta.

EXAMPLE 4

4-(4'-[Indol-3"-yl]thiazol-2'-ylmethyl)-5-methylimidazole (Ar=3-indolyl; HET=4-thiazol-2-yl; n=1; and X=5-methylimidazol-4-yl)

A mixture of 170 mg of indole-3-chloromethyl ketone and 170 mg of 2-(4'-methylimidazol-5'-yl)thioacetamide hydrochloride in 15 ml of isopropanol was heated at reflux for 18 hours. The reaction mixture was cooled, filtered and the filtrate evaporated. The residue was dissolved in ethyl acetate and treated with a solution of ether saturated with hydrogen chloride. The resulting precipitate was filtered and dried, 200 mg.

The NMR (300 MHz, CDCl$_3$) spectrum showed absorption at 2.20 (s, 3H), 4.25 (s, 2H), 7.0–7.4 (m, 4H), 7.45 (s, 1H), 7.65 (s, 1H) and 7.90 (d, 1H) delta.

EXAMPLE 5

Starting with the appropriate alpha halo ketone and requisite thioamide hydrochloride and using the procedure of Example 2, the following compounds were prepared:

| Ar | HET | n | X | NMR (300 MHz, delta) |
|---|---|---|---|---|
| 3-Br-phenyl | thiazole | 1 | CH3-C=C(NH)-N (aminothiazoline) | (DMSO-d$_6$) 2.35 (s, 3H), 4.56 (s, 2H), 7.42 (t, J=8 Hz, 1H), 7.56 (d, J=7 Hz, 1H), 7.95 (d, J=7 Hz, 1H), 8.14 (s, 1H), 8.22 (s, 1H), 9.01 (s, 1H). |
| 4-Br-phenyl | thiazole | 1 | CH3-C=C(NH)-N | (DMSO-d$_6$) 2.36 (s, 3H), 4.56 (s, 2H), 7.64 (d, J=9 Hz, 2H), 7.88 (d, J=9 Hz, 2H), 8.13 (s, 1H), 8.99 (s, 1H). |
| 2-OCH$_3$-phenyl | thiazole | 1 | CH3-C=C(NH)-N | (DMSO-d$_6$) 2.34 (s, 3H), 3.93 (s, 3H), 4.51 (s, 2H), 7.02 (t, J=6 Hz, 1H), 7.13 (d, J=6 Hz, 1H), 7.32 (t, J=6 Hz, 1H), 7.99 (s, 1H), 8.08 (d, J=6 Hz, 1H), 8.31 (s, 1H), 8.98 (s, 1H). |
| 4-F-phenyl | thiazole | 1 | CH3-C=C(NH)-N | (DMSO-d$_6$) 2.36 (s, 3H), 4.53 (s, 2H), 7.27 (t, J=9 Hz, 2H), 7.94 (d, J=6 Hz, 1H), 7.96 (d, J=6 (d, J=6 Hz, 1H), 8.02 (s, 1H), 8.99 (s, 1H) |
| 2-F-phenyl | thiazole | 1 | CH3-C=C(NH)-N | (CDCl$_3$) 2.24 (s, 3H), 4.39 (s, 2H), 7.14 (m, 3H), 7.46 (s, 1H), 7.55 (d, J=2 Hz, 1H), 8.12 (t, 1H). |
| 2-OC$_2$H$_5$-phenyl | thiazole | 1 | CH3-C=C(NH)-N | (CDCl$_3$) 1.48 (t, J=7 Hz, 3H), 2.24 (s, 3H), 4.14 (q, J=7 Hz, 2H), 4.28 (s, 2H), 6.92 (d, J=7 Hz, 1H), 7.00 (t, J=6 Hz, 1H), 7.23 (t, J=6 Hz, 1H), 7.46 (s, 1H), 7.80 (s, 1H), 8.19 (d, J=6 Hz, 1H). |
| 3,5-(CH$_3$O)$_2$-phenyl | thiazole | 1 | CH3-C=C(NH)-N | (CDCl$_3$) 2.26 (s, 3H), 3.85 (s, 6H), 4.30 (s, 2H), 6.44 (t, J=2 Hz, 1H), 7.02 (d, J=3 Hz, 2H), 7.30 (s, 1H), 7.48 (s, 1H). |
| 2-OCH$_3$-naphthyl | thiazole | 1 | CH3-C=C(NH)-N | (CDCl$_3$) 2.27 (s, 3H), 3.89 (s, 3H), 4.38 (s, 2H), 7.26 (m, 4H), 7.43 (s, 1H), 7.54 (d, J=7 Hz, 1H), 7.74 (d, J=7 Hz, 1H), 7.84 (d, J=7 Hz, 1H). |
| 2-OCH$_3$-phenyl | thiazole (5-Me) | 1 | CH3-C=C(NH)-N | (CDCl$_3$) 2.26 (s, 3H), 2.45 (s, 3H), 4.34 (s, 2H), 7.11 (s, 1H), 7.26 (m, 3H), 7.46 (s, 1H), 7.56 (d, J=6 Hz, 1H). |
| 2-CF$_3$-phenyl | thiazole | 1 | CH3-C=C(NH)-N | (CDCl$_3$) 2.20 (s, 3H), 4.26 (s, 2H), 7.19 (s, 1H), 7.44 (s, 1H), 7.51 (m, 3H), 7.70 (d, J=7 Hz, 1H). |

-continued

| Ar | HET | Ar—HET—(CH₂)ₙ—X | | NMR(300 MHz, delta) |
|---|---|---|---|---|
| | | n | X | |
| 3-Cl-C₆H₄— | 5-methyl-thiazol-2-yl | 1 | -C(CH₃)=N-N=CH-NH- (2-aminoimidazole) | (CDCl₃) 2.27 (s, 3H), 4.29 (s, 2H), 7.27 (m, 2H), 7.30 (s, 1H), 7.49 (s, 1H), 7.70 (d, J=7 Hz, 1H), 7.85 (s, 1H). |
| 3-OCH₃-C₆H₄— | 5-methyl-thiazol-2-yl | 1 | " | (CD₃OD) 2.46 (s, 3H), 3.92 (s, 3H) 4.60 (s, 2H), 6.98 (dd, J=1, 10Hz, 1H), 7.38 (t, J=10 Hz, 1H), 7.51 (m, 1H), 7.84 (s, 1H), 7.95 (s, 1H), 8.82 (s, 1H). |
| 3-F-C₆H₄— | 5-methyl-thiazol-2-yl | 1 | " | (CDCl₃) 2.28 (s, 3H), 4.30 (s, 2H), 6.99 (m, 1H), 7.34 (s, 1H), 7.35 (m, 1H), 7.51 (s, 1H), 7.6(m, 2H). |
| 4-CH₃-C₆H₄— | 5-methyl-thiazol-2-yl | 1 | " | (CD₃OD) 2.38 (s, 3H), 2.42 (s, 3H), 4.52 (s, 2H), 7.22 (d, J=7 Hz, 2H), 7.68 (s, 1H), 7.76 (d J=7 Hz, 2H), 8.78 (s, 1H). |
| 4-H₂N-C₆H₄— | 5-methyl-thiazol-2-yl | 1 | " | (CD₃OD) 2.26 (s, 3H), 4.28 (s, 2H), 6.74 (d, J=10 Hz, 2H), 7.32 (s, 1H), 7.61 (s, 1H), 7.62 (d J=10 Hz, 2H). |
| 4-Cl-C₆H₄— | 5-methyl-thiazol-2-yl | 1 | " | (CDCl₃) 2.28 (s, 3H), 4.26 (s, 2H), 7.26 (m, 4H), 7.79 (d, J=6 Hz, 2H). |
| 3-OCH₃-4-HO-C₆H₃— | 5-methyl-thiazol-2-yl | 1 | " | (CD₃OD) 2.26 (s, 3H), 3.86 (s, 3H), 4.29 (s, 2H), 6.74 (dd, J=2, 12 Hz, 1H), 6.93 (d, J=9 Hz, 1H), 7.53 (s, 1H), 7.55 (d, J=2 Hz, 1H), 7.80 (s, 1H). |
| 2-OCH₃-5-F-C₆H₃— | 5-methyl-thiazol-2-yl | 1 | " | (CDCl₃) 2.32 (s, 3H), 3.97 (s, 3H), 4.34 (s, 2H), 6.96 (m, 2H), 7.54 (s, 1H), 7.86 (s, 1H), 7.99 (dd, J=2, 6 Hz, 1H). |
| 2-OCH₃-5-Br-C₆H₃— | 5-methyl-thiazol-2-yl | 1 | " | (DMSO-d₆) 2.29 (s, 3H), 3.88 (s, 3H), 4.48 (s, 2H), 7.07 (d, J=7 Hz, 1H), 7.44 (dd, J=2, 7 Hz, 1H), 8.03 (s, 1H), 8.18 (d, J=2 Hz, 1H), 8.94 (s, 1H). |
| 2,6-di-OCH₃-C₆H₃— | 5-methyl-thiazol-2-yl | 1 | " | (CDCl₃) 2.16 (s, 3H), 3.71 (s, 6H), 4.27 (s, 2H), 6.59 (d, J=7 Hz, 1H), 7.09 (s, 1H), 7.26 (m, 1H), 7.34 (s, 1H). |

| Ar | HET | Ar—HET—(CH₂)ₙ—X | | NMR(300 MHz, delta) |
|---|---|---|---|---|
| | | n | X | |
| 2-methoxyphenyl | 4-methyl-thiazol-2-yl | 1 | 5-methylimidazol-4-yl | (CDCl₃) 2.20 (s, 3H), 2.22 (s, 3H), 3.77 (s, 3H), 4.18 (s, 2H), 6.95 (m, 2H), 7.30 (m, 2H), 7.40 (2, 1H). |
| 1-methoxynaphth-2-yl | 4-methyl-thiazol-2-yl | 1 | 5-methylimidazol-4-yl | (CDCl₃) 2.34 (s, 3H), 3.86 (s, 3H), 4.39 (s, 2H), 7.54 (m, 3H), 7.71 (d, J=8 Hz, 1H), 7.89 (d, J=9 Hz, 1H). |
| 2,5-dimethoxyphenyl | 4-methyl-thiazol-2-yl | 1 | 5-methylimidazol-4-yl | (DMSO-d₆) 2.31 (s, 3H), 3.73 (s, 3H), 3.84 (s, 3H), 4.50 (s, 2H), 6.88 (dd, J=3, 9 Hz, 1H), 7.04 (d, J=9 Hz, 1H), 7.65 (d, J=3 Hz, 1H), 8.0 (s, 1H), 8.97 (s, 1H). |
| 4-bromo-2-methoxyphenyl | 4-methyl-thiazol-2-yl | 1 | 5-methylimidazol-4-yl | (CDCl₃) 2.22 (s, 3H), 2.24 (s, 3H), 3.77 (s, 3H), 4.20 (s, 2H), 6.81 (d, J=8 Hz, 1H), 7.44 (m, 3H). |

EXAMPLE 6

4-(4'-[o-Hydroxyphenyl]thiazol-2-ylmethyl)-3,5-dimethylimidazole (Ar=o-HOC₆H₄; HET=4-thiazol-2-yl; n=1; and X=3,5-dimethylimidazol-4-yl) and 4-(4'-[o-hydroxyphenyl]thiazol-2-ylmethyl)-1,5-dimethylimidazole (Ar=o-HOC₆H₄; HET=4-thiazol-2-yl; n=1; and X=1,5-dimethylimidazol-4-yl)

To a solution of 74 mg of the product of Example 3 in 0.2 ml of tetrahydrofuran cooled in an ice bath was added 41.5 mg of potassium carbonate in 0.2 ml of water, then 0.017 ml of methyl iodide. The reaction mixture was allowed to stir overnight at room temperature, and was then treated with another 0.017 ml of methyl iodide. The mixture was allowed to stir for 3 hours and was then poured into water. The aqueous mixture was extracted several times with chloroform and the extracts combined and dried over sodium sulfate. Removal of the solvent gave 70 mg of an oil. The residue was dissolved in chloroform which was extracted with 2N sodium hydroxide. The organic phase was dried over sodium sulfate and the solvent removed in vacuo. The residue was chromatographed on 5 g of silica gel to give 4.5 mg of the 1,5-dimethyl isomer which had NMR spectrum (300 MHz, CDCl₃) showing absorption at 2.21 (s, 3H), 3.53 (s, 3H), 4.28 (s, 2H), 6.82 (t, J=7 Hz, 1H), 6.96 (d, J=7 Hz, 1H), 7.18 (t, J=7 Hz, 1H), 7.23 (s, 1H), 7.36 (s, 1H) and 7.55 (d, J=7 Hz, 1H) delta and 8.5 mg of the 3,5-dimethyl isomer which had NMR spectrum (300 MHz, CDCl₃) showing sbsorption at 2.26 (s, 3H), 3.52 (s, 3H), 4.32 (s, 2H), 6.86 (t, J=6 Hz, 1H), 6.98 (d, J=6 Hz, 1H), 7.22 (t, J=6 Hz, 1H), 7.34 (s, 1H), 7.41 (s, 1H) and 7.56 (d, J=6 Hz, 1H) delta.

EXAMPLE 7

4-(4''-[1''-Benzylindol-3''-yl]thiazol-2-ylmethyl)-5-methylimidazole (Ar=1-benzylindol-3-yl; HET=4-thiazol-2-yl; n=1; and X=5-methylimidazol-4-yl)

Using the general procedure of Example 2, 400 mg of 1-benzylindole-3-chloromethyl ketone and 270 mg of 2-(4'-methylimidazol-5'-yl)thioacetamide in 50 ml of isopropanol gave, after a reaction time of 18 hours, 400 mg of crude product as a brown solid.

The product was purified by flash chromatography on 10 g of silica gel using chloroform-methanol (20:1-v:v) to give 150 mg of product. The hydrochloride salt was prepared by adding an ethyl acetate solution saturated with hydrogen chloride gas to an ethyl acetate solution of the product, followed by recrystallization from chloroform.

The NMR spectrum (300 MHz, CDCl₃) showed absorption at 2.18 (s, 3H), 4.26 (s, 2H), 5.26 (s, 2H), 7.05–7.16 (m, 9H), 7.42 (s, 1H), 7.62 (s, 1H) and 7.90 (m, 1H) ppm.

EXAMPLE 8

4-(4'-[Phenyl]thiazol-2'-ylmethyl)-1,5-dimethylimidazole (Ar=C₆H₅; HET=4-thiazol-2-yl; n=1; and X=1,5-dimethylimidazol-4-yl)

Phenacyl chloride (270 mg) and 360 mg of 2-(1', 5'-dimethylimidazol-4'-yl)thioacetamide hydrochloride in 15 ml of isopropanol were heated to reflux for 9 hours. The reaction mixture was cooled, the solvent evaporated and the residue diluted with water. The aqueous mixture was extracted with chloroform and the pH of the aqueous solution raised to 9 with 2N aqueous sodium hydroxide. The product was extracted with chloroform and the extracts combined and dried over sodium sulfate. Removal of the solvent provided 350 mg of residue as a yellow oil. The product was purified by flash chromatography on 10 g of silica gel using chloroform-methanol (20:1-v:v), 150 mg.

The NMR spectrum (300 MHz, CDCl$_3$) showed absorption at 2.28 (s, 3H), 3.56 (s, 3H), 4.30 (s, 2H), 7.20–7.40 (m, 5H) and 7.85 (m, 2H) ppm.

EXAMPLE 9

Starting with the appropriate alpha halo ketone and requisite thioamide and employing the procedure of Example 8, the following compounds were prepared:

| Ar | HET | n | X | NMR(300 MHz, delta) |
|---|---|---|---|---|
| 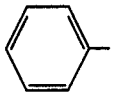 | 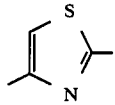 | 1 | 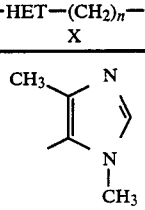 | (CDCl$_3$) 2.16 (s, 3H), 3.50 (s, 3H), 4.30 (s, 2H), 7.20–7.40 (m, 5H), 7.85 (m, 2H). |
| 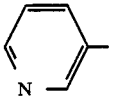 | 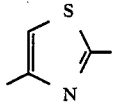 | 1 | 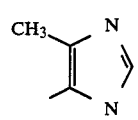 | (CDCl$_3$) 2.16 (s, 3H), 4.28 (s, 2H), 7.30 (m, 1H), 7.38 (s, 1H), 7.52 (s, 1H), 8.10 (d, 1H), 8.50 (d, 1H), 9.02 (s, 1H). |
| 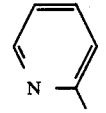 | 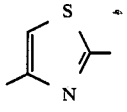 | 1 | 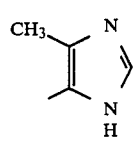 | (CDCl$_3$) 2.16 (s, 3H), 4.23 (s, 2H), 7.10 (m, 1H), 7.40 (s, 1H), 7.65 m, 1H), 7.78 (s, 1H), 7.92 (d, 1H), 8.30 (d, 1H). |
| 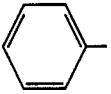 | 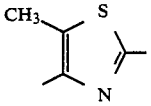 | 1 | 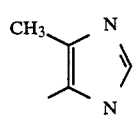 | (CDCl$_3$) 2.16 (s, 3H), 2.50 (s, 3H), 4.22 (s, 2H), 7.25–7.45 (m, 3H), 7.50 (s, 1H), 7.58 (d, 2H). |
| 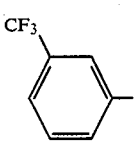 | 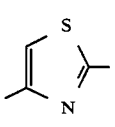 | 1 | 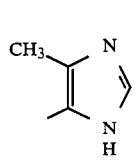 | (CDCl$_3$) 2.24 (s, 3H), 4.30 (s, 2H), 7.45 (m, 3H), 7.90 (m, 2H), 8.01 (s, 1H). |
| 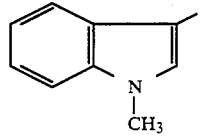 | 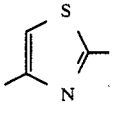 | 1 | 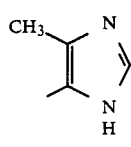 | (DMSO-d$_6$) 2.20 (s, 3H), 3.84 (s, 3H), 4.16 (s, 2H), 7.16 (m, 2H), 7.48 (m, 3H, 7.82 (s, 1H), 8.05 (d, 1H). |
| 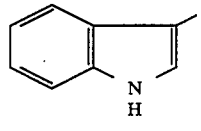 | 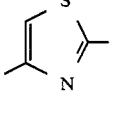 | 1 | 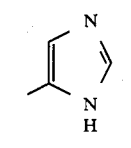 | (DMSO-d$_6$) 4.60 (s, 2H), 7.15 (m, 2H), 7.44 (d, 1H), 7.70 (m, 2H), 7.88 (s, 1H), 8.05 (d, 1H), 9.12 (s, 1H).(HCl salt). |
| 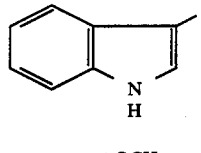 | 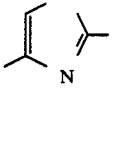 | 2 | 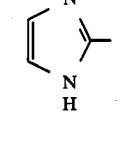 | (DMSO-d$_6$) 3.48 (t, 2H), 3.64 (t, 2H), 7.10 (m, 2H), 7.41 (d, 2H), 7.60 (m, 3H), 7.76 (s, 1H), 7.92 (d, 1H). |
| 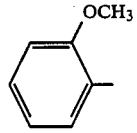 | 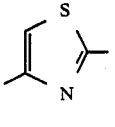 | 1 | 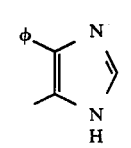 | (CDCl$_3$) 3.90 (s, 3H), 4.50 (s, 2H), 7.0 (m, 2H), 7.25 (m, 2H), 7.36 (m, 2H), 7.52 (s, 1H), 7.56 (m, 2H), 7.72 (s, 1H), 8.15 (d, 1H). |

-continued

| Ar | HET | Ar—HET—(CH$_2$)$_n$—X | | NMR(300 MHz, delta) |
|---|---|---|---|---|
| | | n | X | |
| 2-methoxyphenyl | thiazol-2-yl (S,N) | 1 | imidazol-2-yl (NH) | (DMSO-d$_6$) 3.90 (s, 3H), 4.52 (s, 2H), 6.98 (m, 1H), 7.10 (d, 1H), 7.30 (m, 1H), 7.60 (s, 1H), 7.98 (s, 1H), 8.05 (d, 1H), 9.08 (s, 1H).(HCl salt). |
| phenyl | thiazol-2-yl | 1 | benzimidazol-2-yl | (DMSO-d$_6$) 4.16 (s, 2H), 7.36 (d, 1H), 7.44 (m, 2H), 7.58 (m, 2H), 7.84 (m, 2H), 7.90 (d, 2H), 8.20 (s, 1H).(HCl salt). |
| phenyl | thiazol-2-yl | 1 | 5-methylimidazol-2-yl (NH) | (DMSO-d$_6$) 2.58 (s, 3H), 4.52 (s, 2H), 7.40 (m, 4H), 7.90 (d, 2H), 8.05 (s, 1H).(HCl salt). |
| phenyl | thiazol-2-yl | 2 | imidazol-2-yl (NH) | (DMSO-d$_6$) 3.50 (t, 2H), 3.70 (t, 2H), 7.40 (m, 3H), 7.60 (br.s., 2H), 7.90 d, 2H), 8.0 (s, 1H).(HCl salt). |
| indol-3-yl | thiazol-2-yl | 1 | 1-methyl-5-methylimidazol-2-yl | (CD$_3$OD) 2.36 (s, 3H), 5.62 (s, 2H), 7.10 (m, 3H), 7.38 (m, 2H), 7.52 (s, 1H), 7.71 (s, 1H), 7.94 (d, 1H). |
| phenyl | thiazol-2-yl | 1 | 1-methyl-5-methylimidazol-2-yl | (CD$_3$OD) 2.56 (s, 3H), 5.62 (s, 2H), 7.06 (s, 1H), 7.38 (m, 4H), 7.82 (s, 1H), 7.89 (m, 2H). |

EXAMPLE 10

1-(2'-[o-Methoxyphenyl]thiazol-4-ylmethyl)-5-methylimidazole (Ar=o-CH$_3$OC$_6$H$_4$; HET=2-thiazol-4-yl; n=1; and X=5-methylimidazol-1-yl)

To a solution of 82 mg of 4-methylimidazole in 10 ml of tetrahydrofuran at 5° C. was added 50 mg of sodium hydride in 50% oil and the resulting mixture stirred at 5° C. for 20 minutes. 2-(o-Methoxyphenyl)-4-chloromethylthiazole (240 mg) in 5 ml of the same solvent was added and the reation mixture heated at reflux for 2 hours. The reaction mixture was cooled to room temperature and treated with 1 ml of water. The water and solvent were removed in vacuo and the residue dissolved in chloroform. The chloroform solution was washed with a brine solution, dried over sodium sulfate and concentrated to give 250 mg of crude product. The product was obtained by chromatography on 7 g of silica gel (chloroform-methanol), 40:1-v:v), 100 mg.

The NMR spectrum (300 MHz, CDCl$_3$) showed absorption at 2.25 (s, 3H), 4.01 (s, 3H), 5.22 (s, 2H), 6.80 (m, 1H), 7.10 (m, 3H), 7.35 (m, 1H), 7.55 (d, 1H) and 8.3 (m, 1H) ppm.

EXAMPLE 11

4-(2'-[o-Methoxyphenyl]thiazol-4-ylmethyl)-5-methylimidazole (Ar=o-CH$_3$OC$_6$H$_4$; HET=2-thiazol-4-yl; n=1; and X=5-methylimidazol-4-yl)

A.

1(2'-[Trimethylsilyl]ethoxymethyl-4-methylimidazole

To a suspension of 2.45 g of 50% sodium hydride in oil in 40 ml of tetrahydrofuran and under a nitrogen atmosphere was added a solution of 4.1 g of 4-methylimidazole in 20 ml of the same solvent over a period of 30 minutes. The mixture was stirred at room temperature for 15 minutes and was cooled to 5° C. To the cooled reaction mixture was added slowly 7.31 ml of 2-(trimethylsilyl)ethoxyethyl chloride and the mixture allowed to stir at room temperature for 1 hour. Water (5 ml) was then added and the reaction concentrated to about 10 ml. The residue was dissolved in ethyl acetate which was then washed with water, dried over magnesium sulfate and concentrated to give 10 g of product as an oil.

B.
4-(2'-[o-methoxyphenyl]thiazol-4-ylmethyl)-5-methylimidazole

To a solution of 1.06 g of the product of Example 11A in 20 ml of dry tetrahydrofuran at −78° C. was added 2.4 ml of a 2.5M solution of n-butyl lithium in hexane and the resulting reaction mixture stirred at −78° C. for 15 minutes. To the solution was then added 0.67 ml of trimethylsilyl chloride. After 20 minutes at −78° C. was added 2.4 ml of n-butyl lithium (2.5M) in hexane followed by 1.25 g of 2-(o-methoxyphenyl)-4-chloromethylthiazole in 5 ml of dry tetrahydrofuran. The raction mixture was stirred at −78° C. for 30 minutes and was then allowed to warm to 0° C. Water (1 ml) was added to the reaction mixture and the mixture concentrated in vacuo. The residue was dissolved in chloroform which was then washed with a brine solution and the organic layer separated, dried and concentrated to give 2.5 g of crude product. The product was purified by chromatographing on 60 g of silica gel (chloroformmethanol, 30:1-v:v) to give 300 mg of pure material.

The NMR (300 MHz, $CD_3OD$) spectrum showed absorption at 2.20 (s, 3H), 4.05 (s, 2H), 7.07–7.6 (m, 5H) and 7.97 (s, 1H) ppm (HCl salt).

EXAMPLE 12

4-(4'-[3''-Indolyl]thiazol-2'-ylethyl)-5-methyl imidazole (Ar=3-indolyl; HET=4-thiazol-2-yl; n=2; and X=5-methylimidazol-4-yl)

A.
1-Triphenylmethyl-4-methyl-5-hydroxymethylimidazole

To a solution of 19 g of 4-hydroxymethyl-5-methylimidazole hydrochloride in 350 ml of dimethylformamide was added 36 ml of triethylamine followed in 10 minutes by the addition of 35 g of trityl chloride. A water bath was used to cool the reaction mixture such that it did not rise above 36° C. After stirring at room temperature for 4 hours, the mixture was poured into 1 liter of water and ice. The resulting precipitate was filtered and washed with acetone (2×250 ml) to give 22 g of product.

B.
1-Triphenylmethyl-4-methylimidazole-5-carboxaldehyde

A mixture of 22 g of the product of Example 12A and 33 g of activated manganese dioxide in 800 ml of dioxane was allowed to stir at room temperature for 2 days. The reaction mixture was filtered and the filtrate concentrated to dryness. The residue was triturated with diethyl ether, filtered and dried, 12 g.

C.
3-(1'-Triphenylmethyl-4'-methylimidazole-5'-yl)-acrylonitrile

To a solution of 3.0 g of the product of Example 12B in 30 ml of dry tetrahydrofuran cooled to −50° C. was added 1.4 ml of diethyl cyanomethylphosphate followed by the slow addition of 8.8 ml of a 1M solution of lithium bis(trimethylsilyl)amide in tetrahydrofuran. The reaction mixture was allowed to warm to room temperature for 1 hour. The reaction mixture was diluted with ethyl acetate (30 ml) and washed with water. The organic phase was separated, dried and concentrated to give the product as an oil.

D.
3-(1'-Triphenylmethyl-4'-methylimidazol-5'-yl)-propionitrile

The product of Example 12C and 300 mg of palladium-on-charcoal in 100 ml of ethanol were shaken under a hydrogen atmosphere at 50 psi for 2 days. The spent catalyst was filtered and the filtrate concentrated to give, after trituration with diethyl ether, 1.4 g of the desired product.

E.
3-(1'-Triphenylmethyl-4'-methylimidazol-5'-yl)-thiopropionamide

To a solution of 1.4 g of the product of Example 12D in 10 ml of ethyl acetate was added 0.63 ml of diethyl dithiophosphate followed by the saturation of the reaction mixture with hydrogen chloride. The reaction mixture was stirred at ambient temperature for 18 hours. The reaction mixture was diluted with hexane and purged of hydrogen chloride by the use of nitrogen gas. The product was filtered and dried, 1.6 g.

F.
4-(4'-[3''-indolyl]thiazol-2'-ylethyl)-5-methylimidazole

The product of Example 12E (1.6 g) and 750 mg of indole-3-chloromethyl ketone were added to 20 ml of isopropanol and heated to reflux temperature for 18 hours. The reaction mixture was concentrated and the residue triturated with ethyl acetate. The filtered intermediate was partitioned between ethyl acetate and water at pH 2.5. The aqueous phase was extracted at pH 3 and then adjusted to pH 9.5 and extracted again. The organic phase from the base extraction was dried and concentrated to give the product as an oil. The residue was dissolved in warm ethyl acetate and cooled to room temperature. Ethyl acetate saturated with hydrogen chloride was added to the solution. The precipitate was filtered and recrystallized from isopropanol, 450 mg.

The NMR (300 MHz, $CDCl_3+DMSO-d_6$) spectra showed absorption at 2.10 (s, 3H), 3.05 (t, 2H), 3.32 (t, 2H), 7.15 (m, 3H), 7.38 (d, 1H), 7.46 (s, 1H), 7.68 (s, 1H) and 7.92 (d, 1H) ppm.

EXAMPLE 13

4-(4'-[o-Methoxyphenyl]thiazol-2'-yl)-2-methylimidazole (Ar=o-$CH_3OC_6H_4$; HET=4-thiazol-2-yl; n=0; and X=2-methylimidazol-4-yl)

A. 1-(2'-[Trimethylsilyl]ethoxymethyl-2-cyano 4-methylimidazole

One and four tenths grams of 1-(2'-trimethylsilylethoxymethyl)-2-hydroxymethylimidazole and 5 ml of thionyl chloride were combined and allowed to stir at room temperature for 3 hours. The reaction mixture was diluted with hexane and the precipitate filtered, 900 mg.

To a solution of the filtered product in 15 ml of ethanol was added dropwise a solution of 1.2 g of potassium cyanide in 15 ml of water, the temperature being kept less than 10° C. by cooling. The reaction mixture was allowed to stir at 5°–10° C. for 60 minutes and was then stirred at room temperature for several days. The mixture was diluted with 60 ml of a saturated sodium carbonate solution and was then extracted with ethyl acetate. The ethyl acetate extracts were combined, washed with brine, dried and concentrated to give a dark oil.

The residue was purified by chromatography on 40 g of silica gel (chloroform-ethyl acetate, 2:1-v:v) to give 500 mg of product.

B. 2-Methylimidazole-4-thiocarboxamide

A solution of 500 mg of the product of Example 13A and 0.5 ml of diethyl dithiophosphate was treated with hydrogen chloride. Ethyl acetate (10 ml) was added and the gassing continued. The resulting yellow solution was stirred for 18 hours and was then diluted (10 ml) with hexane. The hexane was decanted from the solids and additional hexane added. The hexane was again decanted and the residue partitioned between ethyl acetate and water adjusted to pH 10. The organic phase was separated, dried and concentrated to give 200 mg of product as an oil.

C. 4-(4'-[o-Methoxyphenyl]thiazol-2'-yl)-2-methylimiazole

A solution of 320 mg of o-methoxyphenacyl bromide and 200 mg of the product of Example 13B in 15 ml of isopropanol was heated at reflux for 2 hours. The reaction mixture was concentrated to a dark oil which was partitioned between ethyl acetate and water at pH 9.5. The organic phase was separated, dried and concentrated to a dark residue. The residual product was purified by chromatographing on 30 g of silica gel using chloroform as the eluent. When the product started to come off the column, the solvent was switched to ethyl acetate. The ethyl acetate fractions were combined and concentrated to give 50 mg of product. The product was dissolved in ethyl acetate and treated with a diethyl ether solution saturated with hydrogen chloride. The solid was triturated with ethyl acetate and filtered, 30 mg.

The NMR (300 MHz, CDCl$_3$) spectrum showed absorption at 2.72 (s, 3H), 3.84 (s, 3H), 6.84 (d, 2H), 7.10 (m, 3H), 7.82 (s, 1H) and 8.24 (d, 1H) (HCl salt).

PREPARATION A

4-Methylimidazol-5-ylthioacetamide

1. 4-Methyl-5-chloromethylimidazole hydrochloride

A solution of 10 g of 4-methyl-5-hydroxymethylimidazole hydrochloride in 25 ml of thionyl chloride was allowed to stir at room temperature overnight. The crystalline product was filtered, washed with chloroform and dried, 11 g.

2. 4-Methyl-5-cyanomethylimidazole

To a solution of 2 g of potassium cyanide in 10 ml of water at 0° C. was added dropwise 1.7 g of the product of Preparation A1 in 30 ml of ethanol. The reaction mixture was stirred at 0° C. for 45 minutes and the solids filtered. The filtrate was combined with 10 ml of a saturated aqueous sodium carbonate solution and the mixture concentrated to dryness. The residue was triturated with hot ethyl acetate and the extracts combined and concentrated to give 950 mg of product as a white solid.

The product was further purified by flash chromatography on 30 g of silica gel using chloroform-methanol (10:1-v:v) as the eluent, 500 mg.

3. 4-Methylimidazol-5-ylthioacetamide hydrochloride

A suspension of 4.1 g of the product of Preparation A2 and 6.31 g of diethyl dithiophosphate in 150 ml of ethyl acetate was saturated with hydrogen chloride gas. The reaction mixture was allowed to stir overnight at room temperature, and the ethyl acetate was decanted from the precipitate. The solids were triturated with hexane and then dissolved in methanol. The methanol solution was concentrated to a foam which solidified on standing, 6.4 g.

PREPARATION B

1,4-Dimethylimidazol-5-ylthioacetamide

1. 1,4-Dimethyl-5-cyanomethyl- and 1,5-dimethyl-4-cyanomethylimidazole

A suspension of 1.17 g of the product of Preparation A2 in 20 ml of dry tetrahydrofuran at 5° C. was treated with 460 mg of sodium hydride (60% in oil) and the mixture stirred at 5° C. for 15 minutes. To the resulting mixture was added 0.6 ml of methyl iodide and the mixture allowed to stir at 5° C. for 30 minutes. The reaction mixture was added to 2 ml of water and the quench concentrated to dryness. The residue was partitioned between 20 ml of ethyl acetate and 20 ml of a brine solution and the organic layer subsequently separated. After repeating the extraction four additional times, the extracts were combined, dried over magnesium sulfate and evaporated to give 1.6 g of a mixture of the titled products. The two isomers were separated by chromatography on 30 g of silica gel using chloroform-methanol (30:1-v:v) to give 820 mg of the 1,5-dimethyl isomer and 240 mg of the 1,4-dimethyl isomer.

2. 1,4-Dimethylimidazol-5-ylthioacetamide hydrochloride

Using the general procedure of Preparation A3, 240 mg of the product of Preparation B1 and 0.3 ml of diethyl dithiophosphate gave 160 mg of the desired product.

PREPARATION C

Imidazol-4-thioacetamide

1. 4-Chloromethylimidazole hydrochloride

Using the procedure of Preparation A1, 5.0 g of 4-hydroxymethylimidazole and 10 ml of thionyl chloride gave 5.0 g of the desired product.

2. 4-Cyanomethylimidazole

Employing the general procedure of Preparation A2, 2.5 g of the product of Preparation C1, 3.2 g of potassium cyanide, 25 ml of water and 25 ml of ethanol gave 340 mg of product.

3. Imidazol-4-ylthioacetamide

A mixture of 340 mg of the product of Preparation C2 and 0.6 ml of diethyl dithiophosphate in 10 ml of ethyl acetate was saturated with hydrogen chloride gas. The solids were filtered and partitioned between water at pH 9.5 and ethyl acetate. The organic phase was separated and the extraction repeated (4×100 ml). The organic layers were combined, dried and concentrated to a solid which was triturated with diethyl ether and filtered, 150 mg.

PREPARATION D

5-Phenylimidazol-4-ylthioacetamide

1. 4-Hydroxymethyl-5-phenylimidazole

To a suspension of 4.5 g of ethyl 5-phenylimidazole-4-carboxylate [J. Het. Chem. 20, 1417 (1983)] in 50 ml of dry tetrahydrofuran at 5° C. was added in portions 1.1 g of lithium aluminum hydride. The resulting reaction mixture was stirred at room temperature for several hours and was then cooled to 10° C. and quenched with 1N hydrochloric acid until the evolution of hydrogen stopped. The reaction mixture was further diluted with water and extracted several times with ethyl acetate. The extracts were combined, dried and concentrated to give a white solid which has triturated with hexane and filtered, 3.2 g.

2. 4-Chloromethyl-5-phenylimidazole hydrochloride

Using the procedure of Preparation A1, 3.2 g of the product of Preparation D1 and 9 ml of thionyl chloride gave the title product which because of decomposition was used immediately in the next reaction.

3. 4-Cyanomethyl-5-phenylimidazole

Using the procedure of Preparaion A2, the product of Preparation D2 and 5.8 g of potassium cyanide in 30 ml of water and 30 ml of ethanol gave 1.2 g of the desired product.

4. 5-Phenylimidazol-4-ylthioacetamide

Employing the procedure of Preparation A3, 1.2 g of the product of Preparation D3 and 1.2 ml of diethyl dithiophosphate in 50 ml of ethyl acetate gave the crude product which was partitioned between ethyl acetate and water adjusted to pH 9.5. The organic phae gave, on evaportaion, 900 mg of the titled product.

PREPARATION E

Benzimidazol-2-ylthioacetamide

Using the procedure of Preparation A3, 2.0 g of 2-benzimidazoleacetonitrile and 2.3 ml of diethyl dithiophosphate in 10 ml of dimethylformamide gave 150 mg of the titled compound.

PREPARATION F

Imidazol-2-ylthiopropionamide

1. 1-(2'-[Trimethylsilyl]ethoxymethylimidazole-2-carboxaldehyde

To 5.5 g of 1-(2'-[trimethylsilyl]ethoxymethyl)-imidazole, prepared by the general procedure of Example 11A, in 20 ml of dry tetrahydrofuran cooled to −70° C. was added 11.2 ml of 2.5M n-butyl lithium in tetrahydrofuran, keeping the temperature below −40° C. The reaction mixture was stirred for 20 minutes at −70° C. followed by the addition of 2.6 ml of dimethylformamide. The reation mixture was allowed to warm to room temperature and to stir over several days. The reaction mixture was treated with water and ethyl acetate. The organic phase was separated, dried and concentrated to an oil, 5.0 g.

2. 1-(2'-[Trimethylsilyl]ethoxymethyl-2-cyanoethylimidazole

Following the procedure of Example 12C/D 3.0 g of the product of Preparation F1, 13 ml of lithium bis(trimethylsilyl)amide (1M solution in tetrahydrofuran) and 2.1 ml of diethyl cyanomethylphosphate in 20 ml of dry tetrahydrofuran gave a product which was hydrogenated using 10% palladium-on-charcoal to give 800 mg of the titled product.

3. Imidazol-2-thiopropionamide

Using the procedure of Preparation A3, 800 mg of the product of Preparation F2 and 0.5 ml of diethyl dithiophosphate in 10 ml of ethyl acetate gave 180 mg of the titled product as the free base.

PREPARATION G

2-Methylimidazol-4-ylthioacetamide

1. Ethyl 2-methyl-1-(2'-[trimethylsilyl]ethoxymethyl)-imidazole-4-carboxylate Using the procedure of Example 11A, 5.0 g of ethyl 2-methylimidazole-4-carboxylate, 1.6 g of 50% sodium hydride and 5.7 g of 2-(trimethylsilyl)ethoxymethyl chloride in 30 ml of dry tetrahydrofuran gave 8 g of the titled product as an oil.

2. 2-Methyl-1-(2'-[trimethylsilyl]ethoxymethyl)-4-hydroxymethylimidazole

Employing the general procedure of Preparation D1, 8.0 g of the product of Preparation G1 and 35 ml of a 1M solution of lithium aluminum hydride in tetrahydrofuran in 50 ml of the same solvent gave 7.5 g of the titled compound.

3. 2-Methyl-1-(2'-[trimethylsilyl]ethoxymethyl)-4-chloromethylimidazole hydrochloride Using the procedure of Preparation A1, 6.0 g of the product of Preparation G2 and 20 ml of thionyl chloride gave 3 g of the desired product.

4. 2-Methyl-1-(2'-[trimethylsilyl]ethoxymethyl)-4-cyanomethylimidazole

Employing the method of Preparation A2, 3.0 g of the product of Preparation G3 and 3.6 g of potassium cyanide in 15 ml of water and 25 ml of ethanol gave 800 mg of the titled product.

5. 2-Methylimidazol-4-ylthioacetamide

Using the procedure of Preparation A3, 800 mg of the product of Preparation G4 and 0.6 ml of diethyl dithiophosphate in 10 ml of ethyl acetate gave 190 mg of the desired product.

PREPARATION H

2-(o-Methoxyphenyl)-4-chloromethylthiazole

1. o-Methoxythiobenzamide

A solution of 6.5 g of o-methyoxybenzonitrile and 8.22 ml of diethyldithiophosphate in 200 ml of ethyl aceate was saturated with hydrogen chloride gas, and the resulting reaction mixture allowed to stir overnight at room temperature. The solvent was removed in vacuo and the oily residue triturated with hexane. The resulting solid was filtered and dried, 3.6 g.

2. 2-(o-Methoxyphenyl)-4-hydroxy-4-chloromethylthiazoline hydrochloride

The product of Preparation H1 (2.7 g) and 2.05 g of 1,3-dichloroacetone in 15 ml of acetone were combined and stirred at room temperature for 18 hours. The resulting precipitate was filtered and dried, 4.5 g.

3. 2-(o-Methoxphenyl)-4-chloromethylthiazole

The product of Preparation H2 (4.3 g) was suspended in 30 ml of methanol and the mixture heated at reflux for 30 minutes. The solvent was removed in vacuo and the residue partitioned between 50 ml of water and 50 ml of ethyl acetate. The pH of the water layer was adjusted to 9 with 3N aqueous hydroxide and the organic layer was separated, dried over magnesium sulfate and concentrated to give the product as a yellow oil, 2.6 g.

We claim:

1. A compound of the formula

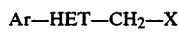

and a pharmaceutically acceptable acid addition salt thereof wherein Ar is pyridyl, 3-indolyl, 8-quinolyl, phenyl or mono- or disubstituted phenyl wherein said substituent is each methyl, methoxy, fluoro, chloro or bromo; HET is thiazolyl; and X is imidazole or mono- or dimethylimidazole.

2. A compound of claim 1, wherein Ar is 3-indolyl and X is 5-methylimidazol-4-yl.

3. The compound of claim 2, 4-(4'-[indol-3-yl]-thiazol-2'-ylmethyl)-5-methylimidazole.

4. A compound of claim 1, wherein Ar is phenyl and X is 5-methylimidazol-4-yl.

5. The compound of claim 4, 4-(4'-phenylthiazol-2'-ylmethyl)-5-methylimidazole.

6. A compound of claim 1, wherein Ar is methoxyphenyl and X is 5-methylimidazol-4-yl.

7. The compound of claim 6, 4-(4'-[o-methoxyphenyl]thiazol-2'-ylmethyl)-5-methylimidazole.

8. A compound of claim 1, wherein Ar is 8-quinolyl and X is 5-methylimidazol-4-yl.

9. The compound of claim 8, 4-(4'-[quinol-8''-yl]thiazol-2'-ylmethyl) -5-methylimidazole.

10. A compound of claim 1, wherein Ar is fluorophenyl and X is 5-methylimidazol-4-yl.

11. The compound of claim 10, 4-(4'-[o-fluorophenyl]thiazol-2'-ylmethyl)-5-methylimidazole.

* * * * *